(12) United States Patent
Worrell

(10) Patent No.: US 10,413,351 B2
(45) Date of Patent: Sep. 17, 2019

(54) SURGICAL DEVICE WITH BIASED KNIFE

(71) Applicant: Ethicon Endo-Surgery, LLC, Guaynabo, PR (US)

(72) Inventor: Barry C. Worrell, Dayton, OH (US)

(73) Assignee: Ethicon LLC, Guaynabo, PR (US)

( * ) Notice: Subject to any disclaimer, the term of this patent is extended or adjusted under 35 U.S.C. 154(b) by 790 days.

(21) Appl. No.: 14/950,975

(22) Filed: Nov. 24, 2015

(65) Prior Publication Data

US 2017/0143408 A1    May 25, 2017

(51) Int. Cl.
*A61B 18/14* (2006.01)
*A61B 17/295* (2006.01)
*A61B 17/29* (2006.01)
*A61B 17/32* (2006.01)

(52) U.S. Cl.
CPC ........ *A61B 18/1445* (2013.01); *A61B 17/295* (2013.01); *A61B 17/320068* (2013.01); *A61B 17/320092* (2013.01); *A61B 2017/2919* (2013.01); *A61B 2017/2922* (2013.01); *A61B 2017/2945* (2013.01); *A61B 2017/2947* (2013.01); *A61B 2017/320069* (2017.08); *A61B 2018/1455* (2013.01)

(58) Field of Classification Search
CPC .... A61B 2018/1455; A61B 2018/1452; A61B 2017/2945; A61B 2018/00601; A61B 17/320092; A61B 17/320093; A61B 17/320095; A61B 17/320097
See application file for complete search history.

(56) References Cited

U.S. PATENT DOCUMENTS

| | | | |
|---|---|---|---|
| 2009/0030440 A1* | 1/2009 | Mastri | A61B 17/29 606/169 |
| 2009/0043305 A1* | 2/2009 | Brodbeck | A61B 18/1445 606/52 |
| 2009/0065552 A1* | 3/2009 | Knodel | A61B 17/072 227/180.1 |
| 2009/0202387 A1 | 8/2009 | Dlugos, Jr. et al. | |
| 2012/0095460 A1* | 4/2012 | Rooks | A61B 17/28 606/45 |
| 2013/0190753 A1* | 7/2013 | Garrison | A61B 17/29 606/41 |
| 2013/0345702 A1* | 12/2013 | Wandel | A61B 18/1445 606/45 |
| 2014/0236152 A1* | 8/2014 | Walberg | A61B 18/1445 606/52 |
| 2015/0082928 A1* | 3/2015 | Kappus | F16H 21/44 74/103 |
| 2016/0270809 A1 | 9/2016 | Boudreaux et al. | |

* cited by examiner

*Primary Examiner* — Eun Hwa Kim
*Assistant Examiner* — Catherine Premraj
(74) *Attorney, Agent, or Firm* — Mintz Levin Cohn Ferris Glovsky and Popeo, P.C.

(57) ABSTRACT

Surgical devices and methods for cutting tissue are provided having a cutting element that is biased to facilitate tissue cutting. For example, a surgical device is provided with a handle that has an elongate shaft assembly with first and second jaws for engaging tissue. The surgical device includes a cutting element that is moveable through a slot formed in at least the second jaw for cutting tissue engaged between the first and second jaws. In an exemplary embodiment, the cutting element is biased toward the second jaw such that the cutting element remains within the slot in the second jaw when thick tissue is engaged.

20 Claims, 7 Drawing Sheets

SURGICAL DEVICE WITH BIASED KNIFE

FIELD

Surgical devices and methods for cutting tissue are provided having a cutting element that is biased to facilitate tissue cutting.

BACKGROUND

Endoscopic surgical instruments are often preferred over traditional open surgical devices since a smaller incision, or incisions, associated with endoscopic surgical techniques tends to reduce the post-operative recovery time and complications, Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applies, access device, drug/gene therapy delivery device, and energy device using ultrasound, RF, laser, etc.).

During surgical procedures, for example, it is often challenging to appropriately engage tissue between jaws of an end effector in order to achieve the desired therapeutic effect. In certain instances, the anatomy of the tissue may hinder the therapeutic effect sought, e.g. thick tissue or tough tissue. While a spring-loaded jaw can assist in accommodating tissue of varying thicknesses, the spring-loaded jaw can deflect during activation of a cutting element resulting in ineffective cutting. Furthermore, the cutting element may deviate from its intended path and can potentially cause harm to the tissue and/or patient, or become jammed within the device.

Accordingly, there remains a need for improved devices and method for cutting tissue provided by a cutting element that is biased to facilitate tissue cutting.

SUMMARY

Various methods and devices are provided for cutting tissue having a cutting element that is biased to facilitate tissue cutting.

In one aspect, a surgical device is provided that includes a housing, an elongate shaft assembly, an end effector, and a cutting element. The elongate shaft assembly extends distally from the housing. The end effector is at a distal end of the elongate shaft, and has first and second jaws movable between an open configuration and a closed configuration. The jaws are effective to engage tissue therebetween, and the first jaw is spring-biased to the closed configuration. The cutting element is movable through a slot formed in at least the second jaw for cutting tissue engaged between the first and second jaws. In an exemplary embodiment, the cutting element is biased toward the second jaw such that, when thick tissue is engaged between the first and second jaws and causes the first jaw to move away from the second jaw against the spring-biased of the first jaw, the cutting element remains within the slot in the second jaw and is effective to cut tissue engaged between the first and second jaws.

The surgical device can vary in any number of ways. For example, the cutting element of the device can include an elongate driver shaft having a knife formed on a distal facing terminal end surface thereof. As another example, the distal portion of the cutting element can have an upper surface that faces the first jaw and that is convexly curved in a proximal-distal direction such that the distal portion of the cutting element has a bowed configuration. In another example, at least a distal portion of the cutting element is pre-bent to be biased toward the second jaw. In still another example, the end effector can include an opening formed in a proximal portion thereof and having the cutting element extending therethrough, the opening biasing the cutting element toward the second jaw. In one embodiment, the opening can be positioned proximal to a pivot point about which the first jaw pivots relative to the second jaw, and the jaw closure shaft can be biased proximally to bias the second jaw toward the first jaw. Additionally, the upper surface of the opening and the upper surface of the cutting element can remain in contact with one another during advancement of the cutting element from a proximal end of the first and second jaws to a distal end of the first and second jaws. The device can also include other features. For example, the housing of the device can include a stationary handle and a movable handle pivotally coupled to the stationary handle. Movement of the movable handle toward the stationary handle can effectively move a yoke coupled to a jaw closure shaft in a proximal direction to thereby pull the second jaw toward the first jaw to the closed configuration. In one embodiment, the first jaw can be in the form of an anvil and the second jaw can include a plurality of staples configured to deform against the anvil. In another example, the first jaw can include a slot formed therein such that a distal tip portion of the cutting element slides longitudinally through the slot in each of the first and second jaws. In still another example, at least one of the first and second jaws can include an electrode for delivering energy to tissue engaged between the jaws.

In another aspect, a surgical device is provided that includes a housing having an elongate shaft extending distally therefrom, a closure assembly extending through the housing and the elongate shaft, and a cutting element. The elongate shaft includes an end effector on a distal end thereof. The closure assembly includes a jaw closure shaft that is movable proximally to pull the first jaw toward the second jaw to the approximated position. The jaw closure shaft can be biased proximally to bias the first jaw to the approximated position. The cutting element is moveable through the first and second jaws for cutting tissue engaged therebetween. The cutting element can be bowed along an upper surface facing the first jaw and the end effector can include a biasing surface formed thereon that contacts the bowed upper surface of the cutting element to bias a distal knife formed on the cutting element toward the second jaw.

The surgical device can vary in any number of ways. For example, the biasing surface can include an opening formed in the end effector, and the cutting element can extend through the opening. As another example, the biasing surface can be located proximal to a pivot point about which the first jaw pivots relative to the second jaw.

In another aspect, a method for cutting tissue is provided that includes engaging tissue between first and second jaws of an end effector on a surgical device. The tissue can cause the first jaw to deflect away from the second jaw. The method also includes actuating a cutting assembly to cause a cutting element to advance through the first and second jaws. The cutting element can be biased toward the second jaw such that, as the first jaw deflects away from the second jaw, the cutting element remains within a slot formed in the second jaw as it advances through the second jaw.

The method can vary in any number of ways. For example, an opening formed in the end effector can contact an upper surface of the cutting element as the cutting element is advanced through the first and second jaws to bias the cutting element toward the second jaw. As another example, the first jaw can be spring-biased toward the second jaw and the tissue can overcome the spring-bias to cause the first jaw to deflect away from the second jaw. In another example, engaging tissue between the first and second jaws can include actuating a trigger on a handle of the surgical instrument to proximally advance a drive shaft coupled to the first jaw. The drive shaft can be biased proximally to thereby bias the first jaw toward the second jaw.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Figure 1:
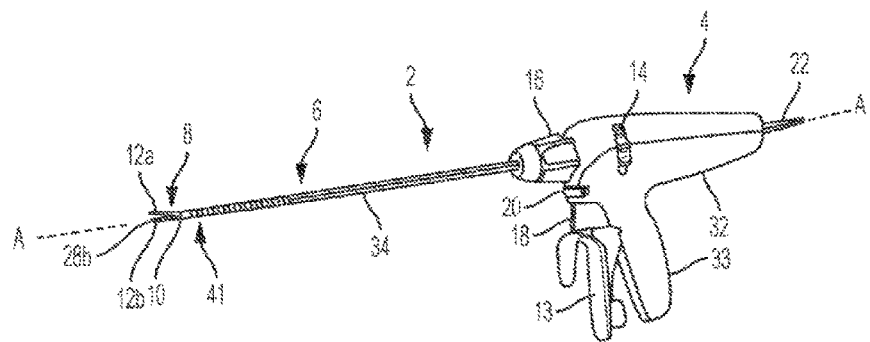
FIG. 1 is a side perspective view of one embodiment of a surgical device.
Figure 2:
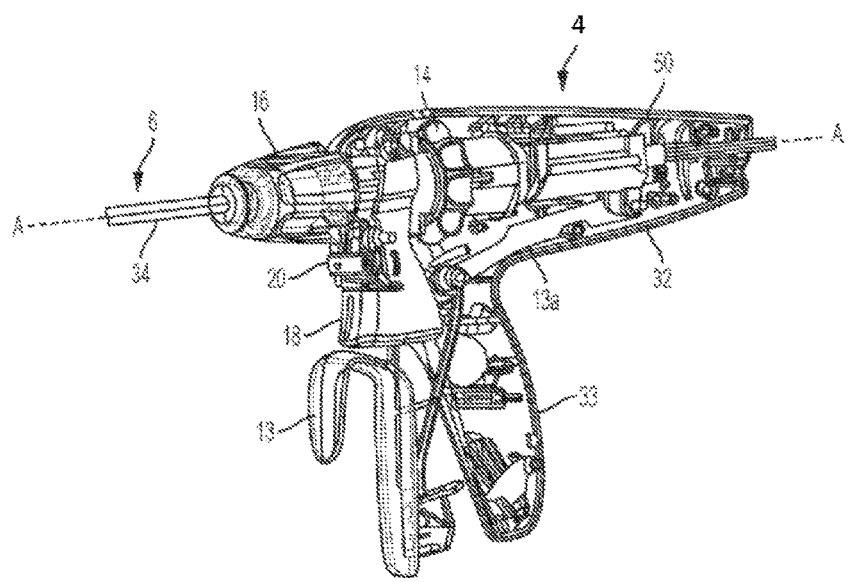
FIG. 2 is a side perspective view of a proximal portion of the surgical device of FIG. 1 with select elements of the surgical device omitted for clarity of illustration.
Figure 3:
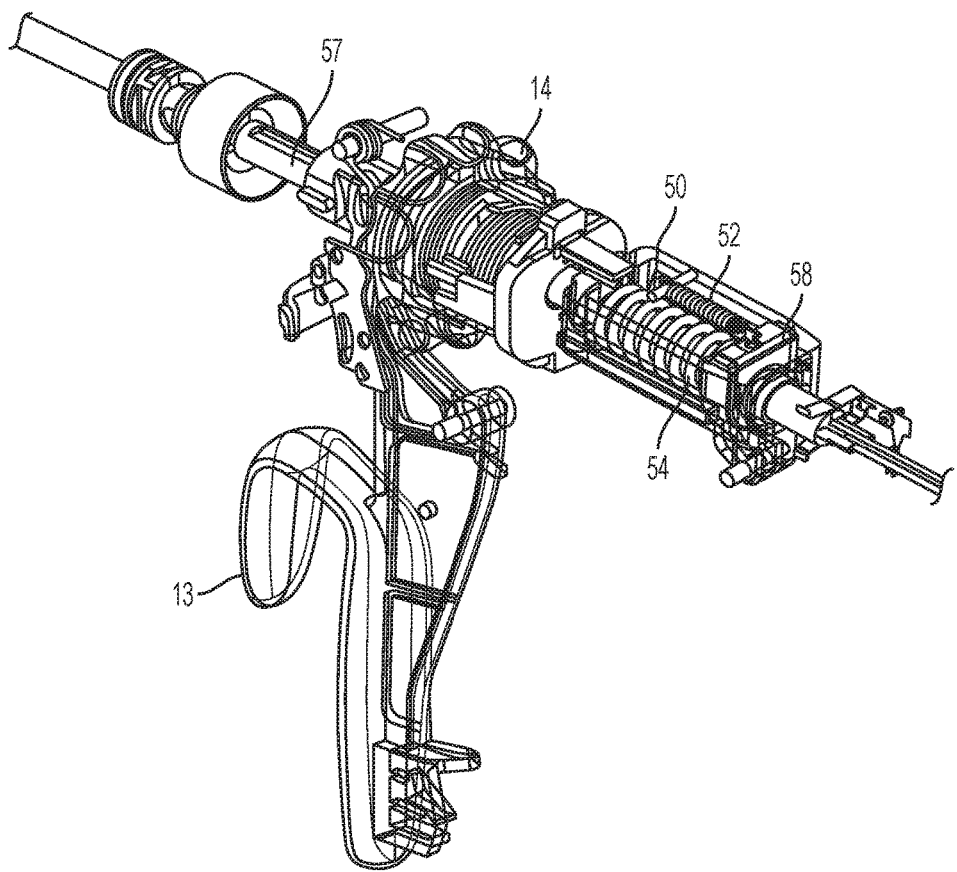
FIG. 3 is another side perspective view of a jaw closure assembly of the surgical device of FIG. 1.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices for cutting tissue are provided and include a cutting element that is biased to facilitate tissue cutting. In general, a surgical device is provided that includes a housing, an elongate shaft assembly, an end effector, and a cutting element. The elongate shaft assembly extends distally from the housing. The end effector is at a distal end of the elongate shaft, and has first and second jaws movable between an open configuration and a closed configuration. The jaws are effective to engage tissue therebetween, and the first jaw is spring-biased to the closed configuration. The cutting element is movable through a slot formed in at least the second jaw for cutting tissue engaged between the first and second jaws. In an exemplary embodiment, the cutting element is biased toward the second jaw such that, when thick tissue is engaged between the first and second jaws and the tissue causes the first jaw to move away from the second jaw against the spring-biased of the first jaw, the cutting element remains within the slot in the second jaw and is effective to cut tissue engaged between the first and second jaws. Such a configuration can significantly reduce the deviation of the cutting element when engaging anatomically difficult tissue.

FIG. 1 illustrates one embodiment of a surgical device 2 that includes a proximal handle portion 4 having a shaft assembly 6 extending distally therefrom. The surgical device 2 includes a working element, referred to herein as an end effector 8, coupled to a distal end of the shaft assembly 6. The illustrated end effector 8 is coupled to the shaft assembly 6 by an articulation joint 10 however a pivot joint or a fixed connection can also be used. Exemplary embodiments of the surgical device 2 are further described in U.S. application Ser. No. 14/658,944 entitled "Methods And Devices For Actuating Surgical Instruments" filed on Mar. 16, 2015, which is hereby incorporated by reference herein in its entirety.

Figure 7A:
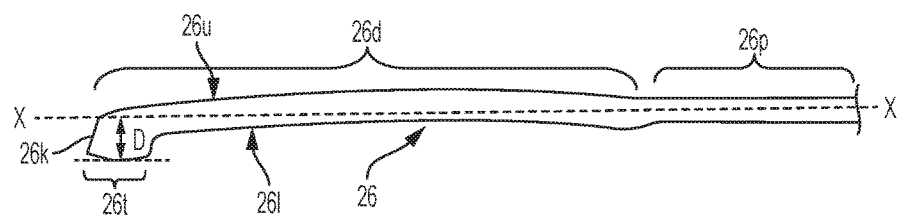
FIG. 7A is a side view of the cutting element included in the cutting assembly of the surgical device of FIG. 1.
Figure 7B:
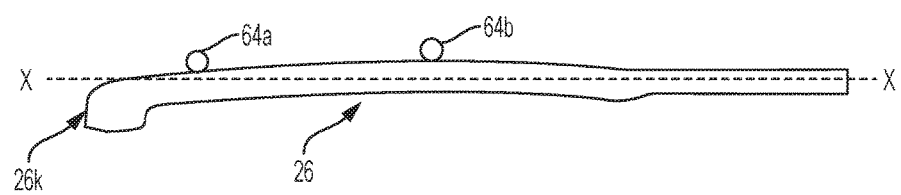
FIG. 7B is a side view of the cutting element included in the cutting assembly of the surgical device of FIG. 1 showing contact points during advancement of the cutting element.
Figure 7C:
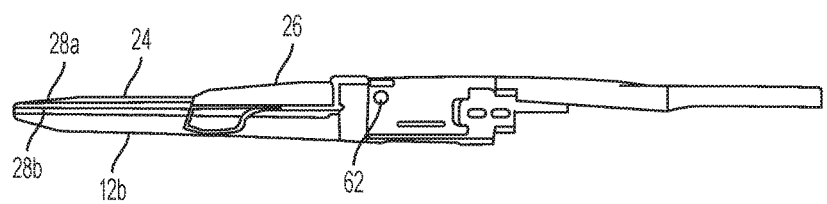
FIG. 7C is a side view of the cutting element and various components of the end effector of the surgical device of FIG. 1.
Figure 8A:
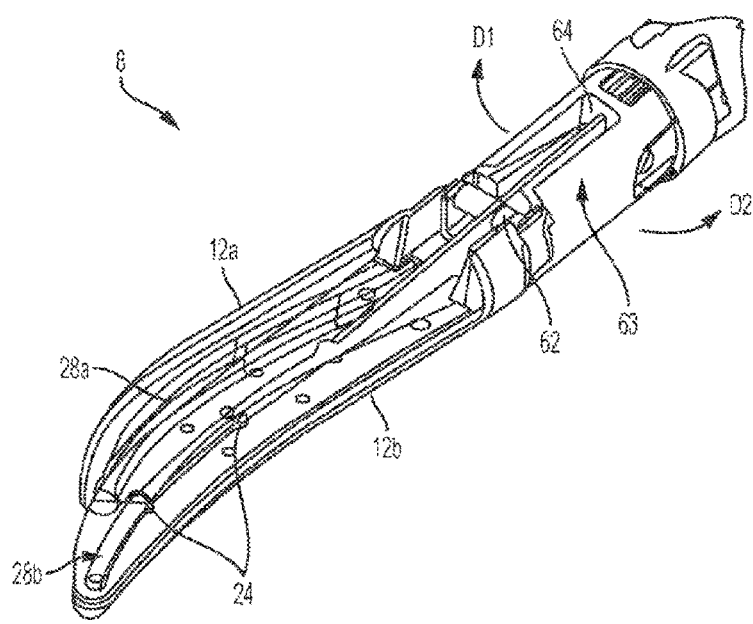
FIG. 8A is a top perspective view of a distal portion of the surgical device of FIG. 1 with select elements partially transparent.

The end effector 8 can have a variety of sizes, shapes, and configurations. As shown in FIG. 1, the end effector 8 has a first and second upper and lower jaws 12a, 12b that are movable between open and closed positions for engaging tissue therebetween. The jaws 12a, 12b each include an elongate slot or cutting pathway 28a, 28b therein (as shown in FIGS. 7C and 8A) through which a cutting element 26 can be configured to slide via the shaft assembly 6. The end effector 8 can have other configurations, e.g. scissors, a babcock, a retractor, etc. In an exemplary embodiment, the first upper jaw 12a is movable relative to the lower jaw 12b, which remains stationary. In other embodiments, only the lower jaw 12b can move or both jaws 12a, 12b can move.

One or both of the jaws 12a, 12b can include a plurality of electrodes 24 (as shown in FIG. 8A), which can be configured to contact tissue positioned between the jaws 12a, 12b and to apply energy thereto. As shown in FIG. 8A, the electrodes 24 are arranged longitudinally along the lower jaw 12b, but the electrodes 24 can be arranged in any of a variety of ways on the upper jaw 12a and/or lower jaw 12b. The electrodes 24 include at least one positive electrode and at least one negative electrode that are coupled to a generator and/or an equivalent energy source via electrical leads extending through the shaft assembly 6 and the proximal handle portion 4.

The proximal handle portion 4 can have a variety of sizes, shapes, and configurations. The handle portion 4 can include a main housing 32 and a stationary handle 33, which can house a variety of elements therein. The handle portion 4 can also include various actuators, such as a first actuator or closure trigger 13, a second actuator or articulation knob 14, a third actuator or rotation knob 16, a fourth actuator or knife trigger 18, and a fifth actuator or energy button 20, as shown.

The first actuator or closure trigger 13 can be configured to effect the opening and closing of the jaws 12a, 12b, e.g. movement of the jaws 12a, 12b toward and away from one another. The jaws 12a, 12b in FIG. 1 are shown in the open position. In the illustrated embodiment, the upper jaw 12a is configured to move relative to the lower jaw 12b, which can remain stationary relative to the shaft assembly 6. In other embodiments, in order to effect the opening and closing of the end effector 8, the lower jaw 12b can be configured to move relative to the upper jaw 12a, or both the upper and lower jaws 12a, 12b can be configured to move relative to the shaft assembly 6.

In an exemplary embodiment, the closure trigger 13 is in the form of a gripper arm or U-shaped trigger. The closure trigger 13 can have different sizes, shapes, and configurations, e.g., no thumb rests, multiple finger loops, different arcuate shape, etc. As shown in FIGS. 1-3, 5B, and 6B, the closure trigger 13 is pivotally attached to the main housing 32. The closure trigger 13 can be configured to move toward and away from a stationary handle on the main housing 32, thereby causing opening and closing the jaws 12a, 12b of the end effector 8, as discussed further below.

The second actuator 14 can be configured to effect articulation of the end effector 8, e.g., movement of both jaws 12a, 12b in a same direction relative to a longitudinal axis "A" of the shaft assembly 6. The articulation can be independent of the opening and closing of the jaws 12a, 12b. The end effector 8 in FIG. 1, is shown in an unarticulated position, e.g. at a zero angle relative to the longitudinal axis "A". The second actuator 14 can be operatively connected to an actuation mechanism, which can be disposed within the main housing 32 and is discussed further below, such that actuation of the second actuator 14, e.g., manual movement thereof by a user, can cause articulation of the end effector 8. In an exemplary embodiment, the second actuator 14 can be configured to be actuated so as to cause the jaws 12a, 12b to articulate in opposite directions D1, D2 (as shown in FIG. 8A) relative to the longitudinal axis "A".

The second actuator 14 can have a variety of sizes, shapes, and configurations. In the illustrated embodiment, the second actuator 14 is in the form of a rotatable knob. Rotation of the second actuator 14 in one direction (e.g., clockwise) can be configured to cause articulation of the end effector 8 in a first direction D1 (e.g., right) and rotation of the second actuator 14 in the opposite direction (e.g., counterclockwise) can be configured to cause articulation of the end effector 8 in a second direction D2 (e.g., left). The knob 14 can include one or more finger depressions on an exterior surface thereof, as shown. The finger depressions can facilitate manual movement of the knob 14 using one or more fingers seated in the finger depressions. As in this illustrated embodiment, the finger depressions can extend around an entire circumference of the knob's exterior surface. While not shown, the knob 14 can extend through and be accessible on both sides of the handle portion 4 to accommodate left and right handed users.

The rotation knob 16 can be configured to rotate the shaft assembly 6 and the end effector 8 about the longitudinal axis "A" of the shaft assembly 6. The illustrated rotation knob 16 is in the form of a circular disc disposed on a proximal end of the shaft assembly 6 and coupled to a distal end of the handle portion 4. The rotation knob 16 can be rotated about the longitudinal axis "A", but the rotation knob 16 can have a variety of other configurations, e.g., a lever, a button, a movable handle, etc. In the illustrated embodiment, the rotation knob 16 is configured to continuously and repeatedly rotate the shaft assembly 6 and the end effector 8 a full 360° in both a clockwise and counterclockwise direction. In other words, the shaft assembly 6 can be configured for unlimited bi-directional rotation. As will be appreciated by a person skilled in the art, the shaft assembly 6 and the end effector 8 can be rotated less than 360° as desired during performance of a surgical procedure (e.g., rotated 20°, rotated 90°, rotated 150°, etc.) and can be rotated more than 360° as desired during performance of a surgical procedure (e.g., rotated 450°, rotated 480°, rotated 720°, etc.).

The fourth actuator or knife trigger 18 can be configured to translate a cutting element 26 (e.g., a knife, a blade, etc.) along the end effector 8. The cutting element 26, as shown in FIGS. 7A-7C, can be configured to cut tissue positioned between the jaws 12a, 12b, as discussed further below. As shown in FIG. 7A, the jaws 12a, 12b each include a cutting pathway 28a, 28b therein through which the cutting element 26 can be configured to slide.

The surgical device 2 can also be configured to apply energy to tissue, such as radiofrequency (RF) energy or ultrasound energy. The handle portion 4 can have a power cord 22 extending proximally therefrom that can be configured to supply energy to the surgical device 2, such as by connecting to a generator. The energy button 20 can be configured to turn on and off the application of the energy, which can be delivered to tissue via the electrodes 24. The energy button 20 can be operatively connected to a conductive lead (not shown), which includes an RF cable, configured to be in electrical communication with the power cord 22 and with the electrodes 24. Actuation of the energy button 20, e.g., pushing the button, can be configured to close a circuit and thereby allow power to be provided to the RF cable, which can accordingly allow power to be supplied to the electrodes 24. The energy button 20 is in the form of a button in the illustrated embodiment, but the energy button 20 can have other configurations, e.g., a knob, a lever, a moveable handle, a switch, etc. In other embodiments, the surgical device 2 need not be configured to apply energy to tissue.

The shaft assembly 6 can have a variety of sizes, shapes, and configurations. The shaft assembly 6 can have any longitudinal length, although in an exemplary embodiment it can be long enough to allow the handle portion 4 to be manipulated outside a patient's body while the shaft assembly 6 extends through an opening in the body with the end effector 8 disposed within a body cavity, e.g., having a longitudinal length of about 33 centimeters (cm). In this way, the end effector 8 can be easily manipulated when the surgical device 2 is in use during a surgical procedure. The shaft assembly 6 can have any diameter. For example, the shaft assembly's diameter can be less than or equal to about 15 millimeters (mm), e.g., less than or equal to about 10 mm, less than or equal to about 7 mm, less than or equal to about 5 mm, etc. which can allow for insertion of the shaft assembly 6 through a minimally invasive access device. The end effector 8 mated to the shaft assembly's distal end can have a diameter equal to or less than the shaft assembly's diameter, at least when the jaws 12*a*, 12*b* are in the closed position, which can facilitate insertion of the device's distal portion into a patient's body.

In the illustrated embodiment, the shaft assembly 6 can include an outer elongate shaft 34 (also referred to herein an "outer shell") and at least one actuation shaft extending between the handle portion 4 and the end effector 8. The one or more actuation shafts can be configured to facilitate articulation of the end effector 8, to facilitate opening/closing of the end effector 8, and/or to facilitate movement of the cutting element 26 along the end effector 8.

In an exemplary embodiment, the surgical device 2 can include first and second actuation shafts configured to facilitate articulation of the end effector 8, a third actuation shaft configured to facilitate opening/closing of the end effector 8, and a fourth actuation shaft configured to facilitate movement of the cutting element 26 along the end effector 8. In other embodiments, a surgical device can include any combination of actuation shafts configured to facilitate articulation of the end effector, opening/closing of the end effector, and movement of the cutting element along the end effector. The actuation shafts can each have relatively small diameters, which can facilitate their inclusion in a device configured to be used in a minimally invasive surgical procedure. In an exemplary embodiment, the outer shell 34 can have a diameter in a range of about 0.2 inches to 0.221 inches.

As indicated above, the closure trigger 13 is effective to open and close the jaws 12*a*, 12*b* of the end effector 8. While various techniques can be used to effect movement of the jaws in response to movement of the closure trigger 13, in the illustrated embodiment the closure trigger 13 is coupled to a yoke 50 by a linkage 13*a* and the yoke 50 in turn is coupled to a closure tube or shaft. Movement of the closure trigger 13 toward the stationary handle 33 is effective to move the yoke 50 proximally, thereby moving the closure tube or shaft proximally to pull the upper jaw 12*a* closed.

Figure 4:
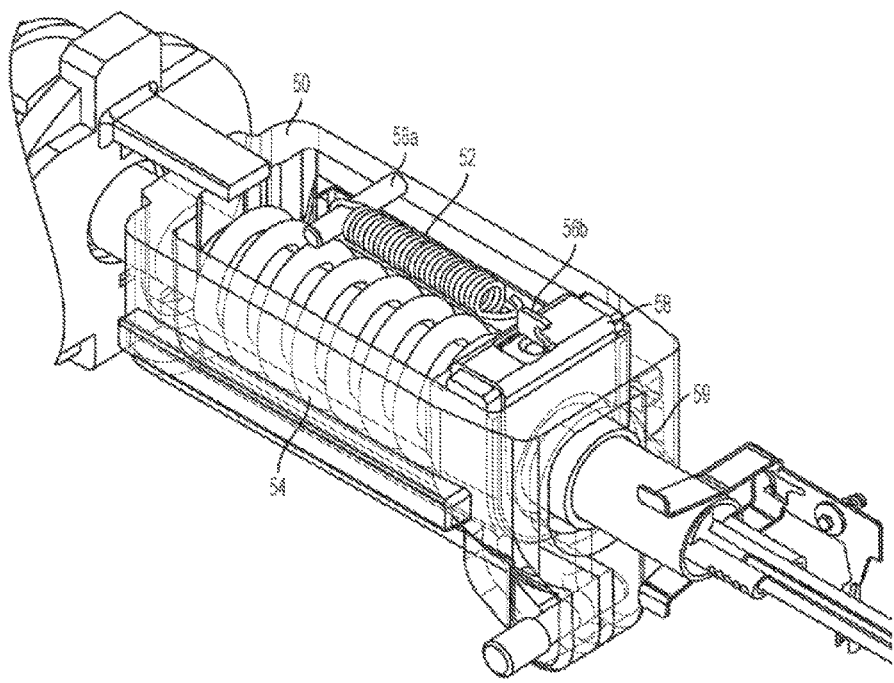
FIG. 4 is a side perspective view of portions of the jaw closure assembly of FIG. 3.

As also indicated above, the upper jaw 12*a* can be spring-biased toward the closed position to allow deflection of the upper jaw 12*a* away from the lower jaw 12*b* when thick tissue is engaged therebetween. The spring-bias is provided by a return spring 52, a compression spring 54, and a spring plate 58, as shown in more detail in FIGS. 3 and 4. The spring plate 58 is mated to an actuation shaft or jaw closure shaft 57 such that the spring plate 58 and the jaw closure shaft 57 move together. The compression spring 54 is disposed within the yoke 50 and compresses between one end of the yoke 50 and the spring plate 58. Movement of closure trigger 13 toward the stationary handle 33 moves the linkage 13*a* proximally, thus moving the yoke 50 proximally. When the yoke 50 is moved proximally to close the jaws, the compression spring 54 becomes compressed thereby applying a proximally-directed force to the spring plate 58. This force will cause the spring plate 58 and the jaw closure shaft 57 mated thereto to move proximally, thereby pulling the upper jaw 12*a* to the closed position. The compression spring 54 will continue to bias the upper jaw 12*a* to the closed position, however when thick tissue is engaged between the jaws 12*a*, 12*b*, the tissue may overcome the spring bias and cause the upper jaw 12*a* to at least partially open. When the closure trigger 13 is released, the return spring 52 will function to return the components to the initial position. As shown, the return spring 52 is coupled at one end to the main housing 32, e.g., by a fixed peg 56*a* on the main housing 32, and at the other end to the spring plate 58, e.g., by a fixed hook 56*b* on the spring plate 58. As a result, the return spring 52 will apply a distal pulling force to the spring plate 58 to pull the spring plate 58 and thus the jaw closure shaft 57 to the initial distal position, in which the jaws 12*a*, 12*b* are in the open configuration. While the illustrated return spring 52 and compression spring 54 are linear springs configured to move between compressed, equilibrium, and/or stretched positions, the springs 52, 54 can have other configurations, e.g., torsion spring, garter spring, conical compression spring, magazine spring, double torsion spring, spring ring, etc.

Figure 5A:
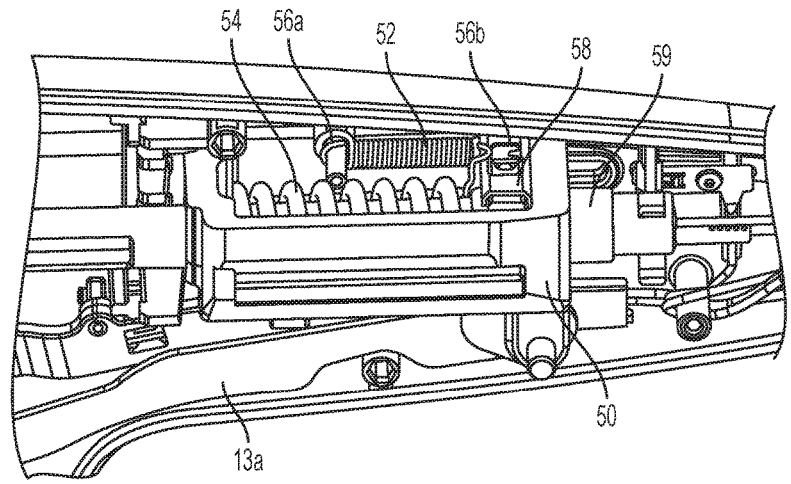
FIG. 5A is a side view of a proximal portion of the surgical device of FIG. 1 showing the jaw closure and knife advancing components when the end effector is in the open configuration.
Figure 5B:
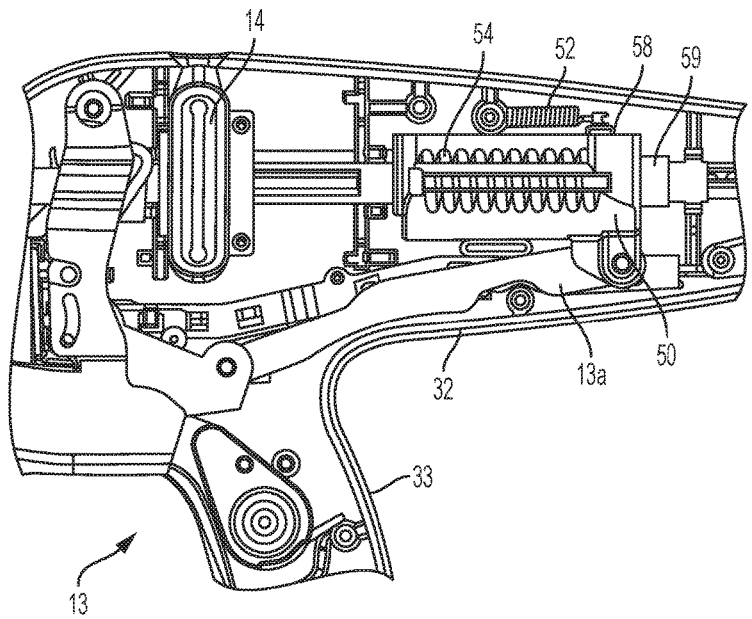
FIG. 5B is another side view of the proximal portion of the surgical device of FIG. 1 showing the jaw closure and knife advancing components when the end effector is in the open configuration.

FIGS. 5A and 5B illustrate the yoke 50 when the jaws 12*a*, 12*b* of the surgical device 2 are in the open position (as shown in FIG. 1). In this position, the return spring 52 maintains the jaw closure assembly in the initial, open configuration. An outer shell 59 is exposed when the yoke 50 is in the open position. In this illustrated embodiment, the closure trigger 13 is positioned to be away from the main housing 32, thereby keeping the end effector 8 open.

Figure 6A:
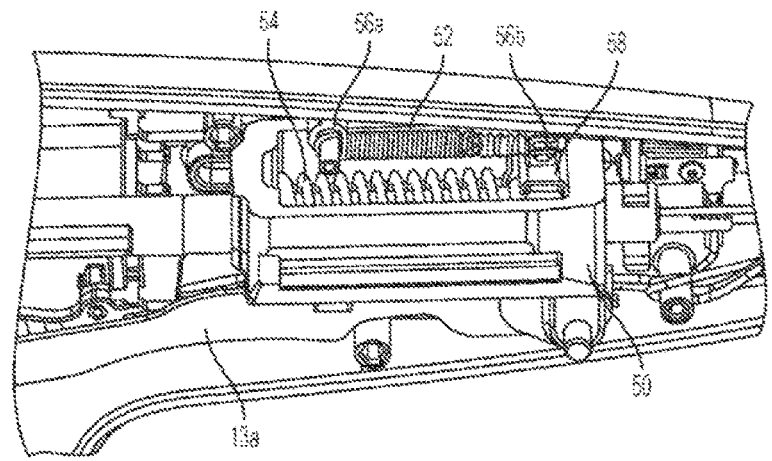
FIG. 6A is a side view of a proximal portion of the surgical device of FIG. 1 showing the jaw closure components when the end effector is in the closed configuration.
Figure 6B:
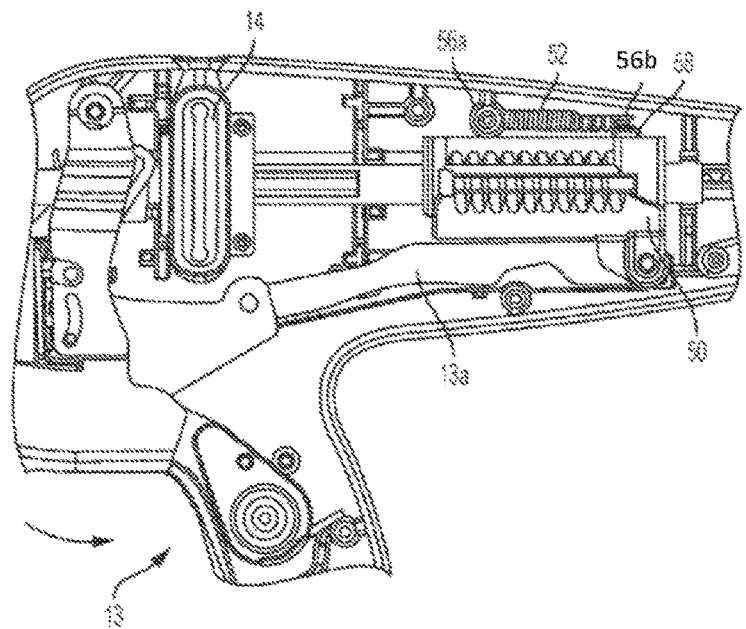
FIG. 6B is another side view of the proximal portion of the surgical device of FIG. 1 in the closed configuration.

FIGS. 6A and 6B illustrate the yoke 50 when the jaws 12*a*, 12*b* of the surgical device 2 are in the closed position. The closure trigger 13 is moved toward the stationary handle 33, and the jaws 12*a*, 12*b* of the end effector 8 are in the closed configuration. The yoke 50 has moved proximally and has slid over the outer shell 59, thereby concealing the outer shell 59. In this position, the compression spring 54 is compressed between the yoke 50 and the spring plate 58, and is thus biasing the spring plate 58 and the jaw closure shaft 57 proximally to bias the upper jaw 12*a* to the closed position. The return spring 52 is in a stretched position and thus applies a pulling force to the spring plate 58.

Once the closure trigger 13 has been activated and the jaws are in the closed position, the cutting assembly can be utilized to cut tissue engaged between the jaws. While not discuss herein, the closure trigger 13 and stationary handle 33 can include locking features to maintain the closure trigger 13 in the actuated position, with the jaws closed.

During certain surgical procedures, thick and/or tough tissue may cause the spring-loaded jaw engaging the tissue to deflect during the activation of the cutting element. Deflection of the spring-loaded jaw can hinder effective cutting of the engaged thick tissue. Alternatively, when the spring-loaded jaw does not fully close and engage the tissue, the activated cutting element may deviate from its intended cutting pathway and become jammed within the surgical device and/or cause irrevocable harm to the engaged tissue and/or patient.

As indicated above, the activation of the knife trigger 18 translates the cutting element 26 along the end effector 8 through the cutting pathway 28*a*, 28*b* in each of the jaws 12*a*, 12*b*. As shown in FIGS. 7A-7C, the cutting element 26 is configured to cut tissue positioned between the jaws 12*a*, 12*b*, as discussed further below. When the cutting element 26 is passed through the cutting pathways 28*a*, 28*b*, the upper surface of the cutting pathway 28*a* in the upper jaw 12*a* and the lower surface of the cutting pathway 28*b* in the lower jaw 12b will maintain the cutting element 26 therebetween. However, when the upper jaw 12a is caused to deflect away from the lower jaw 12b, e.g., due to thick tissue, the cutting pathway 28a in the upper jaw 12a will no longer contact the upper surface of the cutting element 26. As a result, the cutting element 26 may slide up and over the tissue engaged between the jaws, or it can otherwise deviate from the intended cutting path. Accordingly, to avoid this, in an exemplary embodiment, the cutting element 26 can be biased toward the lower jaw 12b, e.g., into the cutting pathway 28b in the lower jaw 12b, so as to stay within the cutting pathway 28b to effectively cut tissue engaged between the jaws.

The cutting element 26 can have a variety of sizes, shapes, and configurations. FIGS. 7A-7C illustrate an exemplary cutting element 26 that has a generally elongate configuration and that is formed from a spring steel material. A proximal portion 26p of the cutting element 26 can have a length that is sufficient to extend through the entire length of the shaft assembly 6 and to couple via various gears or other mechanisms to the knife trigger 18 on the proximal handle portion 4. A distal portion 26d of the cutting element can have a length that is substantially the same as or greater than a length of the jaws 12a, 12b of the end effector, and the distal portion 26d can include a sharp cutting surface or knife 26k formed on the distal-facing surface thereof for cutting tissue engaged between the jaws 12a, 12b. As indicated above, the shape of the distal portion 26d can be configured to bias the distal-most end having the knife 26k thereon toward the lower jaw 12b. While this can be achieved using various techniques, in one aspect the cutting element 26 itself can have a shape that biases the cutting element into the lower jaw 12b. In particular, as shown, the distal portion 26d of the cutting element 26 can have an upper surface 26u that is convexly curved in a proximal-distal direction along the length thereof, and the lower surface 26l of the distal portion 26d can have a concave curvature in the proximal-distal direction. As a result, the distal portion 26d can have a generally bowed configuration. The distal-most tip 26t of the distal portion 26d can also be overly bent such that the upper surface 26u (at the distal-most tip 26t) is positioned closer to a longitudinal axis X of the cutting element 26 than the lower surface 26l (at the distal-most tip 26t) of the cutting element 26. In an exemplary embodiment, the lower surface 26l at the distal-most tip 26t is positioned a distance D from the longitudinal axis X, and the distance can be in the range of about 1 to 3 mm. This can result in the lower surface at the distal-most tip 26t from being about 0.44 mm lower than a standard cutting element known and used in the art. As shown in FIG. 7C, when the cutting element 26 is advanced at least partially through the lower jaw 12b, the lower surface 26l at the distal-most tip 26t will be biased into and will extend all the way into the cutting pathway 28b in the lower jaw 12b.

Figure 8B:
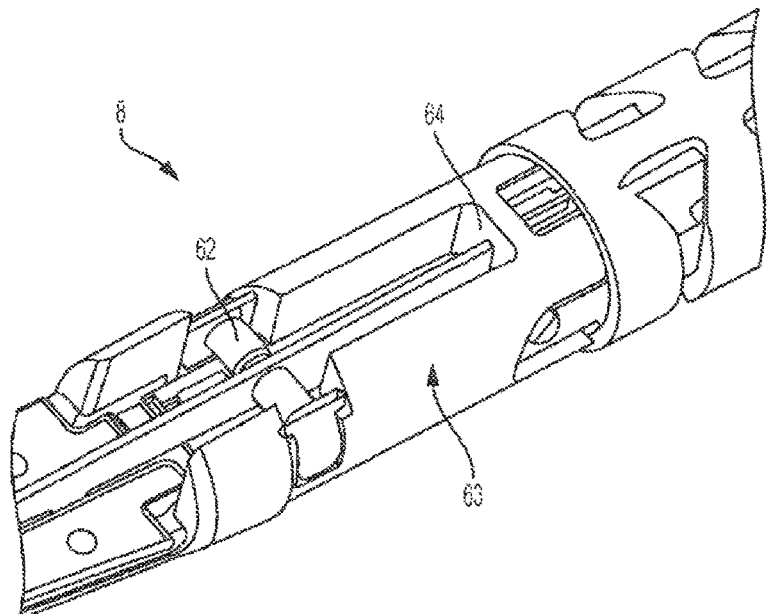
FIG. 8B is another top perspective view of the distal portion of the surgical device of FIG. 1 with select elements partially transparent.

In addition, or as an alternative, to having the cutting element 26 be shaped to create a spring-bias toward the lower jaw 12b at the distal portion 26d of the cutting element 26, the end effector 8 itself can include features to bias the distal portion 26d toward the lower jaw 12b. As shown in FIGS. 8A and 8B, the end effector 8 can include a proximal housing 63 having the lower jaw 12b fixedly coupled to or integrally formed therewith and extending distally therefrom, and having the upper jaw 12a pivotally coupled thereto. As shown, a pivot pin 62 extends through the proximal housing 63 of the end effector 8 and through the upper jaw 12a to allow the upper jaw 12a to pivot thereabout. The proximal housing 63 can also include a lumen 64 extending therethrough for receiving at least the cutting element 26. The lumen 64 is located proximal to the pivot pin 62 such that movement of the upper jaw 12a does not interfere with the lumen 64. An upper surface of the lumen 64 can abut against an upper surface 26u of the cutting element 26, as shown in FIGS. 8A and 8B. Since the upper surface 26u of the distal portion 26d of the cutting element 26 is convexly curved in the proximal-distal direction, as the cutting element 26 is advanced through the lumen 64, the upper surface of the lumen 64 will push the cutting element 26 down toward lower jaw 12b within the cutting pathway 28b. FIG. 7B illustrates the contact location of the upper surface of the lumen 64 in the end effector as the cutting element 26 is advanced therethrough. In particular, the upper surface of the lumen 64 contacts the cutting element 26 at contact point 64a when the cutting element 26 is in the proximal position, i.e., it has not been advanced through the jaws. When the cutting element 26 is advanced distally through the jaws, the upper surface of the lumen 64 contacts the cutting element 26 at contact point 64b. As shown, contact point 64b is located further away from the longitudinal axis X then contact point 64a. Since the lumen 64 in the end effector will not move relative to the longitudinal axis and thus the contact points 64a, 64b will remain stationary, the cutting element 26 instead will be forced to move away from the longitudinal axis and toward the lower jaw 12b depending on its position relative to the lumen 64. In particular, when the cutting element 26 is in its fully extended position, the lumen 64 will be at contact point 64b and will have an increased downward force on the cutting element 26 as compared to the force applied to the cutting element when it is in its initial retracted position and the lumen 64 is at contact point 64a.

As indicated above, the device disclosed herein can be used to engage and cut tissue, and to optionally deliver energy to the tissue. In an exemplary method, the device is introduced into a body cavity, e.g., through an incision, an access port, or through a natural orifice, and the jaws are positioned adjacent to tissue to be treated. With tissue positioned between the jaws, the closure trigger 13 can be actuated to move the upper jaw 12a toward the lower jaw 12b to engage tissue therebetween. The spring-bias applied to the upper jaw 12a will allow the upper jaw 12a to move away from the lower jaw 12b in response to thick tissue engaged therebetween. Once the tissue is engaged, the knife trigger 18 can be actuated to advance the cutting element through the jaws 12a, 12b for cutting tissue engaged therebetween. The pre-bent configuration of the cutting element 26 will bias the distal-most tip 26t toward the lower jaw 12b. The bowed upper surface of the cutting element 26 will also work in coordination with the lumen 64 in the proximal housing of the end effector 8 to bias the distal-most tip 26t toward the lower jaw 12b. In particular, the upper surface of the lumen 64 formed in the proximal housing 63 of the end effector 8 will contact the upper surface 26u of the cutting element 26 as the cutting element 26 advances through the jaws 12a, 12b to bias the cutting element 26 toward the lower jaw 12b. In the event that the upper jaw 12a, which is spring-biased toward the lower jaw 12b, deflects away from the lower jaw 12b due to thick tissue, the cutting element 26 will remain in the cutting pathway 28b in the lower jaw 12b. Thus, regardless of the position of the upper jaw 12a, the cutting element 26 will remain in the cutting pathway 28b in the lower jaw 12b through the entire cutting stroke to effectively cut the tissue engaged between the jaws. During or after cutting is complete, the energy button 20 can be activated to deliver energy to the tissue.

A person skilled in the art will appreciate that the present invention has application in conventional minimally-invasive and open surgical instrumentation as well as application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular components and subsequent reassembly. In particular, the device can be disassembled, and any number of the particular components or parts of the device can be selectively replaced or removed in any combination. Upon cleaning, sterilizing, and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, sterilizing, cleaning, replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the device is placed in a closed and sealed container, such as a plastic or TYVEK® bag. The container and device are then placed in a field of radiation that can penetrate the container, such as gamma radiation, x-rays, or high-energy electrons. The radiation kills bacteria on the device and in the container. The sterilized device can then be stored in the sterile container. The sealed sterile container keeps the device sterile until it is opened in the medical facility.

Typically, the device is sterilized. This can be done by any number of ways known to those skilled in the art including beta or gamma radiation, ethylene oxide, steam, and liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method of Sterilizing An Implantable Medical Device". It is preferred that the device, if implanted is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical instrument, comprising:
   a housing;
   an elongate shaft extending distally from the housing;
   an end effector at a distal end of the elongate shaft, the end effector having first and second jaws movable between an open configuration and a closed configuration in which the jaws are effective to engage tissue therebetween, the first jaw being spring-biased to the closed configuration; and
   a cutting element movable distally through a slot formed in the first and second jaws for cutting tissue engaged between the first and second jaws, an upper surface of the slot contact an upper surface of the cutting element to apply a biasing force to the cutting element toward the second jaw such that, when thick tissue is engaged between the first and second jaws and causes the first jaw to move away from the second jaw against the spring-bias of the first jaw, the cutting element remains within the slot in the second jaw and is effective to cut tissue engaged between the first and second jaws,
   wherein the biasing force of the upper surface of the slot on the cutting element increases as the cutting element moves distally through the slot.

2. The surgical instrument of claim 1, wherein the cutting element comprises an elongate driver shaft having a knife formed on a distal facing terminal end surface thereof.

3. The surgical instrument of claim 1, wherein the upper surface of the cutting element has distal portion that faces the first jaw and that is convexly curved in a proximal-distal direction such that the distal portion of the cutting element has a bowed configuration.

4. The surgical instrument of claim 1, wherein at least a distal portion of the cutting element is pre-bent to be biased toward the second jaw.

5. The surgical instrument of claim 1, wherein the end effector includes an opening formed in a proximal portion thereof and having the cutting element extending therethrough, the opening biasing the cutting element toward the second jaw.

6. The surgical instrument of claim 5, wherein the opening is positioned proximal to a pivot point about which the first jaw pivots relative to the second jaw.

7. The surgical instrument of claim 5, wherein an upper surface of the opening contacts the upper surface of the cutting element to bias the cutting element toward the second jaw, the upper surface of the cutting element being oriented toward the first jaw.

8. The surgical instrument of claim 7, wherein the upper surface of the opening and the upper surface of the cutting element remain in contact with one another during advancement of the cutting element from a proximal end of the first and second jaws to a distal end of the first and second jaws.

9. The surgical instrument of claim 1, wherein the housing includes a stationary handle and a movable handle pivotally coupled to the stationary handle, movement of the movable handle toward the stationary handle being effective to move a yoke coupled to a jaw closure shaft in a proximal direction to thereby pull the second jaw toward the first jaw to the closed configuration.

10. The surgical instrument of claim 9, wherein the jaw closure shaft is biased proximally to bias the second jaw toward the first jaw.

11. The surgical instrument of claim 1, wherein at least one of the first and second jaws includes an electrode for delivering energy to tissue engaged between the jaws.

12. The surgical instrument of claim 11, wherein the biasing surface comprises an upper surface of an opening formed in the end effector, the cutting element extending through the opening.

13. The surgical instrument of claim 11, wherein the biasing surface is located proximal to a pivot point about which the first jaw pivots relative to the second jaw.

14. The surgical instrument of claim 1, wherein the cutting element is configured to be biased toward the second jaw such that the cutting element is forced to move away from a longitudinal axis of the elongate shaft and toward the second jaw when the cutting element is advanced distally through the second jaw.

15. The surgical instrument of claim 1, wherein the upper surface of the cutting element is a spring-biased surface that is configured to bias the cutting element toward the second jaw.

16. The surgical instrument of claim 11, wherein the bowed upper surface of the cutting element is shaped to create a spring-bias toward the second jaw.

17. The surgical instrument of claim 11, wherein the bowed upper surface of the cutting element extends along an entire length of the second jaw when the cutting element is fully advanced distally through the second jaw.

18. The surgical instrument of claim 11, wherein the biasing surface of the end effector has a first contact protrusion and a second contact protrusion positioned to contact the bowed upper surface of the cutting element to bias the distal knife toward the second jaw, only the first contact protrusion biasing the distal knife in the proximal-most position, both the first and second contact protrusions biasing the distal knife in the distal-most position, the second contact protrusion being spaced distally away from the first contact protrusion along a longitudinal axis of the elongate shaft.

19. The surgical instrument of claim 11, wherein the biasing surface of the end effector contacts an upper-most point of the bowed upper surface of the cutting element to bias the distal knife toward the second jaw in the proximal-most position.

20. A surgical instrument, comprising:
a housing having an elongate shaft extending distally therefrom with an end effector on a distal end thereof, the end effector including a first jaw that is pivotally coupled to a second jaw and that is movable from a spaced position to an approximated position in which the first and second jaws are configured to engage tissue therebetween;
a closure assembly extending through the housing and the elongate shaft, the closure assembly having a jaw closure shaft that is movable proximally to pull the first jaw toward the second jaw to the approximated position, the jaw closure shaft being biased proximally to bias the first jaw to the approximated position; and
a cutting element movable through the first and second jaws from a proximal-most position to a distal-most position for cutting tissue engaged therebetween, the cutting element being bowed along an upper surface facing the first jaw and the end effector including a biasing surface formed thereon configured to contact the bowed upper surface of the cutting element to bias a distal knife formed on the cutting element toward the second jaw, the biasing surface biasing the distal knife toward the second jaw in the proximal-most position such that the distal knife is biasing only toward the second jaw in the proximal-most position.

\* \* \* \* \*